US009660953B2

(12) United States Patent
Smith

(10) Patent No.: US 9,660,953 B2
(45) Date of Patent: *May 23, 2017

(54) SYSTEM FOR PROVIDING CONTINUOUS VIEWABLE INDICIA FOR REMINDERS AND FOR INDUCING VIEWER ACTIONS

(71) Applicant: Johnathon Smith, Shafter, CA (US)

(72) Inventor: Johnathon Smith, Shafter, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/951,428

(22) Filed: Nov. 24, 2015

(65) Prior Publication Data

US 2016/0080311 A1 Mar. 17, 2016

Related U.S. Application Data

(63) Continuation-in-part of application No. 13/179,445, filed on Jul. 8, 2011, now Pat. No. 9,195,967.

(60) Provisional application No. 61/362,586, filed on Jul. 8, 2010.

(51) Int. Cl.
| G09G 3/00 | (2006.01) |
| H04L 12/58 | (2006.01) |
| G06F 19/00 | (2011.01) |
| H04L 12/24 | (2006.01) |
| G06Q 10/10 | (2012.01) |
| H04L 13/18 | (2006.01) |

(52) U.S. Cl.
CPC .......... *H04L 51/36* (2013.01); *G06F 19/3456* (2013.01); *G06Q 10/107* (2013.01); *G06Q 10/109* (2013.01); *G06Q 10/1097* (2013.01); *G09G 3/00* (2013.01); *G09G 3/004* (2013.01); *G09G 3/008* (2013.01); *H04L 13/188* (2013.01); *H04L 41/026* (2013.01); *H04L 51/24* (2013.01)

(58) Field of Classification Search
CPC . G05B 19/042; G06F 17/3087; G06F 19/327; G06F 3/011; G06F 3/0325; G06F 3/0425; G06Q 10/06; G06Q 10/107; G06Q 10/109; G06Q 10/1097; G06Q 30/02; G08G 1/0962; G08G 1/09671; G09B 3/00; G09F 7/04; H04H 60/78; H04N 5/74; H04W 8/30; G09G 3/00; G09G 3/004; G09G 3/008; H04L 41/026; H04L 13/188

See application file for complete search history.

(56) References Cited

U.S. PATENT DOCUMENTS

| 5,528,263 A * | 6/1996 | Platzker | G06F 3/011 345/156 |
| 6,760,045 B1 * | 7/2004 | Quinn | G06F 17/30873 707/E17.111 |
| 6,922,155 B1 * | 7/2005 | Evans | G08G 1/0962 340/4.6 |

(Continued)

Primary Examiner — Le H Luu
(74) Attorney, Agent, or Firm — Donn K. Harms

(57) ABSTRACT

A system for providing patients with dementia or other cognitive impairment with instructions and reminders of tasks to enable them to live with minimum third party oversight. The system provides for a continuous display of viewable indicia of at least one of text or images to provide the patient messages. The messages may be generated by a remote third party or software running on a computer. Employing the system, a remote user such as the child of a patient can provide instruction and reminders to the patient allowing them to live with minimal supervision.

17 Claims, 5 Drawing Sheets

(56) References Cited

U.S. PATENT DOCUMENTS

| | | | | |
|---|---|---|---|---|
| 7,675,504 B1* | 3/2010 | Smith | ............... | G06F 3/0325 345/156 |
| 2001/0045037 A1* | 11/2001 | Bank | ............... | G09F 7/04 40/621 |
| 2002/0005821 A1* | 1/2002 | Park | ............... | G06Q 30/02 345/30 |
| 2003/0085929 A1* | 5/2003 | Huber | ............... | G05B 19/042 715/810 |
| 2004/0138925 A1* | 7/2004 | Zheng | ............... | G06Q 10/06 705/2 |
| 2005/0168705 A1* | 8/2005 | Li | ............... | H04N 5/74 353/69 |
| 2006/0167617 A1* | 7/2006 | Krikelis | ............... | G08G 1/096716 701/117 |
| 2006/0253365 A1* | 11/2006 | Langshur | ............... | G06F 19/327 705/37 |
| 2007/0253350 A1* | 11/2007 | Tung | ............... | H04H 60/78 370/312 |
| 2008/0026356 A1* | 1/2008 | Kagan | ............... | G09B 3/00 434/322 |
| 2009/0215436 A1* | 8/2009 | Howard | ............... | H04W 8/30 455/414.3 |
| 2010/0194976 A1* | 8/2010 | Smith | ............... | G06F 3/0425 348/373 |
| 2011/0047583 A1* | 2/2011 | Howard | ............... | H04W 8/30 725/109 |

* cited by examiner

SYSTEM FOR PROVIDING CONTINUOUS VIEWABLE INDICIA FOR REMINDERS AND FOR INDUCING VIEWER ACTIONS

This application is a Continuation in Part patent application to U.S. patent application Ser. No. 13/179,445 filed on Jul. 8, 2011, which claims priority to U.S. Provisional Patent Application 61/362,586 filed on Jul. 8, 2010, both of which are included herewith in their respective entirety by reference thereto.

BACKGROUND OF THE INVENTION

1. Field of the Invention

The present invention relates generally to personal message devices. More particularly, the disclosed system herein relate to a device and method to provide a viewer, with one-way and interactive messaging and information visually or through oral communication should the recipient be visually impaired. The communications in the form of messages and information are provided on displays on walls or screens and is unalterable by the viewer, and/or may be provided through local broadcast using a loudspeaker.

The communications to the viewer are provided remotely in real time and also in predetermined time frames. The system thereby provides third parties such as relatives, or caretakers a means to convey information including one or a combination of images, text, date counters, visual and audible reminders, and other informational input, whereby the remote recipient, such as an elderly relative, may read and view the information on a screen or other projected image or the like, positioned so as to catch their attention in both a direct and periphery view. The information communicated and displayed may be controlled and transmitted remotely over a network connection, such as via a personal computer over the internet or using by a smartphone. The information can also be communicated in an audible fashion to the recipient, should they be visually impaired, and/or to augment the visual depiction of the information.

2. Prior Art

Computers, phones, and other multimedia devices are ever evolving providing users access to virtual spaces where convenience, connectivity, and social awareness are incorporated into the daily lives of the users. Many devices such as smart phones and personal computers employing social networking and messaging capabilities, provide viewers and users means for real-time interactive communication and messaging, thereby allowing a user to feel involved, connected, organized, and informed about daily going-ons of friends, loved ones, relatives, and more.

Such electronic and virtual informational communication tools additionally provide means for users to personally manage their often fast pace lives. Upcoming and prior events can be tracked, schedules can be organized, and memories enhanced through the provision of communication, imaging and the like, and all at the touch of a button. Smart phones, tablets, and PCs access and interconnect the virtual space often through wireless high speed internet connection allowing access from almost anywhere in the world.

With such an advance in technology there is inevitability a greater advance in technological know-how required for the users. Although many users of such smart devices and internet connected communications systems do not necessarily require an in-depth computer programming skill set, there can be a continuing need to learn new steps and methods. However, since most technology has only been recently developed, there is certainly a learning curve and ability needed to operate and navigate through the applications and devices providing these many useful services.

The use and involvement with such communications technology and services, while highly beneficial, may be difficult however for those users or viewers who have with mental and physical disabilities, or lack the technical or worldly sophistication required. For instance, young children can lack the knowledge to effectively operate such systems. Another group who could benefit from such communications and technological systems are the elderly, however they may be challenged to operate the system due to mental, visual, or other reasons, or may have days when they are challenged and days when they are perfectly adept in running and benefiting from such a system.

For individuals who have an ongoing cognitive or physical disability, or for those individuals who may have a transient cognitive problem, the employment of visual and/or audible interactive communications and computerized systems can be a significant aid to their daily regimen. Consequently, with the appropriate information and communications managed by third parties alone, or in combination with the challenged user, they may lead independent, social, and organized lives.

As such, it is a shame that such individuals are not afforded access to such virtual communications and information systems due to a transient or ongoing cognitive disability or the like wherein access thereto would provide a richer, fuller, life. For example, images, texts, sounds, singularly or in combinations thereof, can be displayed in the homes of dementia patients for reminders of medication regiments, family visits, important dates, etc. or young children can have friendly reminders about homework, class schedules, chores, etc.

As such there is a continuing and unmet need for a system employing devices and methods allowing for visual and/or audible social networking, communication, and messaging information including text, images, events, and the like, for such cognitively challenged individuals. Such a system should provide for visual and audible messages and for indicia and images to be displayed in a manner enabling it to be constantly viewed and accessible to an individual in their home or other domicile.

The visual and/or audible communication of information should be easily changed and updated remotely, in concert with the sender, or employing multiple users such as caretakers, family members, or friends. The system should provide convenient reminders of events, dates, and schedules to name a few. The device and method should preferably need no interaction from the remote viewer and be easy to use. As noted, the information can be communicated as audible sound for users who are visually impaired or to augment the visually communicated information to the remote recipient thereof.

The system should be able to provide real time and up to date indicia and information in concert with ongoing displayed images and text, through positioning or projecting such as on walls or surfaces which the viewing party constantly passes or views, or in audible fashion in areas occupied, to increase the chance of the communication reaching the cognitively challenged viewer, and should employ a means for depicting the video which is not alterable by the viewer nor can it be turned off by the remote viewer.

SUMMARY OF THE INVENTION

The device and method herein disclosed and described provides a solution to the shortcomings in prior art and achieves the above noted goals through the provision of a remotely updated, automated, one-way or interactive, multimedia personal message board display, and/or using audible sound, with fixed, random, and timed messaging, configured as a reminder/memory aid. The device and method provides a means for dynamic display or audible communication of important messages, alerts, schedules, social events, and more in the form of text, images, sounds, or combinations thereof. Individuals unable to access such multimedia via conventional means such as PCs, smart phones, or tablets are now afforded the ability to stay connected and up to date with things such as family matters and social happenings via the message board display device and audible sound of the present invention.

The device generally includes a display means, such as preferably a planar depiction from a flat screen display or a projector projecting images on a wall or screen in the home or office. Such a display means provides advantages in that individuals unable to employ smart phones, PCs, or the like due to disabilities, difficulty with dexterity or vision, are provided a relatively large display easily seen and employable in the home. The display, however, may be on a television screen, PC, cell phone, smart phone, or tablet in combination with or separately from a projector type display. The display may also be interactive such as via sensing devices, employed throughout the users home or office, or via wirelessly controlled electronics. As noted earlier, sound may be communicated to the same locale to augment the visual display, or for recipients of such information who may be temporarily or permanently visually impaired.

The display means provides conveyance of information such as alerts of upcoming events, reminders of past events, and other relative information such as current day and time. Varying information and messages may be displayed in separate windows or sections of the overall display to provide organization of information as needed. There device may additionally scroll through multiple windows and display themes and modes or contain static information depending on user defined management controls and settings.

The information displayed or audibly communicated is preferably managed remotely through wireless connection such as the INTERNET or similar means via communication with a PC, cell phone, smart phone, tablet, or the like. There may also be a local server providing access such as via a website or the like wherein users may access and manage the information to be displayed 24 hours a day, 7 days a week. The intended recipient or other users, such as caretakers, parents, or the like may access the management of the communicated displayed and/or audible information on a real time basis, setting event and alert priorities, personal messages/images, urgent messages, and upcoming schedules of events to name a few.

Although the present device and method can be employed with an almost infinite number of uses, a few of the particularly preferred modes of employment of the device and system are outlined shortly below. As these examples are merely shown to convey the overall intended scope and purpose of the device, they should as such not be considered limiting to the many possible additional means of employment of the device and method herein.

For a first example, a parent may employ the device in the room of a child wherein a first portion of the projected display on a screen or other planar surface, indicates a wake-up time accompanied by a sound. Additionally on another portion of the depicted screen may be a list of tasks to complete in the morning with pictures or images adjacent text, such as brushing teeth, making the bed, completing homework, eating breakfast, etc. However, the display may include any text, image, sound or combination thereof and is not limited to task oriented subjects but may simply be stories, Bible verses, poems, jokes, uplifting messages, etc. Sound communication of information using a loudspeaker would be especially beneficial for visually impaired individuals, or to augment the visual display of such information for recipients who comprehend better with multiple modes of concurrent communication of the same information.

It is within the intended scope of the device to provide real time communication of displayed and if required audible transmission of information. If the child is not at the breakfast table by a certain time, the parent, via a phone, PC, or the like may send an instantaneous urgent message to the display within the child's room further indicating to 'WAKE UP' or 'Breakfast is Ready!', for example. Different task may be individually prioritized to increase the visibility and hence noticeability of the task as needed. For example, if the child often forgets to make their bed, then a related message may occur more frequently on portions of the display.

As a second example, the device may be employed within the home or assisted living space of a dementia patient. The device and information provided audibly and/or on the planar display of the device can help aid in solving or preventing many of the problems associated commonly with dementia such as but not limited to abandonment/loneliness, constant questions/confusion/curiosity, re-asking for items that take time to acquire, food/medication regiments, paranoia/unreasonable expectations, pain/mood at certain times of day, decision making, and inability to find things/can't remember where things are. Displayed information should be on a planar video display or projected to a surface that is visible to the remote cognitively impaired viewer, yet is also unalterable. Further, the protected images and text and other indicia, should be in a position which the impaired viewer is most likely to view at the remote location. Indicia displayed can provide step by step instructions for daily tasks, medical and eating regiments, and reminders of upcoming and past events, and family member names, phone numbers, and addresses. It can include a section for immediate reminders or instructions. As noted sound may also communicate the information singularly for visually impaired recipients, or concurrently with the visually displayed information to help augment full understanding of such the recipient.

The device may include different modes of depicting the display that work together to keep the user engaged and informed and as noted may include sound which concurrently audibly communicated the information depicted on the display. By increasing the users's confidence and self sufficiency, the user may stay at home longer without assistance than if they did not have the message board display of the present invention.

If the viewer is sufficiently cognitive to operate in an tactile or audibly interactive mode of the device, it may help the user feel more connected, allowing them to be happier and more content. Using the appropriate subset of modes, based off the cognitive and physical ability of the remote viewer, the projected message board and/or sound communications can use these modes to aid the user as needed. It becomes a reminder, as well as an entertainment device, while encouraging the viewer to become more active and involved.

There may be included a message mode, such as providing a visually depicted and/or audible uplifting messages or the like, giving the user sense of well-being if supplied with appropriate information. This may keep the user calmer especially in times of confusion and it may give him/her more confidence in what is going on, because he/she feels like they know. Other messages may be reminders of previous and upcoming visits from family members and loved ones, social events, telephone conversations, and the like. Such reminders can beneficially provide a means of maintaining the user in an active state of remembering things/events wherein normally the user would forget immediately and get into a state of confusion. To provide further reminders and alerts, events and the like may be set at different priorities and include hour/day counters leading up to and following an event as a past reminder. This may be an advantage for dementia or similar patients having trouble remember upcoming as well as immediately past events.

In the case of communication of the message in an audible manner to the recipient, the voice used to communicate the information may be changed to suite the information being communicated. For example, a recognizable voice of a family member or friend may be employed to communicate an audible uplifting message. However, a non familiar voice may be used to communicate a command or reminder so that the recipient performs a task based on an authoritative command versus the same information from a family member voice which might be ignored.

Additionally included may be a full screen mode, which serves to break up the monotony of the message mode thus increasing the effectiveness of the device. The system may communicate visual cues to jog memory by showing personal pictures, phrases, quotes, etc. This mode can also be used as a mood elevator by displaying text/stories that the viewer would appreciate and enjoy. Again, depending on the information being communicated, a family voice or an authoritative voice might be used to gain the attention of the recipient.

Additionally included may be an urgent alert mode, which serves to aid the care giver, family member, or the like, in helping the user from a distance. Such a visual and/or audible alert display is both simple to understand but distracting enough to grab attention. Such alert indicators may be reminders that a phone is ringing, the stove was left on, the front door is open/unlocked, etc, wherein varies sensors are employed throughout the users house and communicate with the device accordingly. Such communication may be wired or wireless communication as needed.

Still further included may be a medication mode, which serves to aid the remote recipient user or viewer, and the care giver, by reminding for the dispensing of medication and allowing the sending of confirmations if medication was taken to the care giver, if appropriate hardware is in place.

Forgetfulness with elderly and dementia patient regarding medication can be deadly when not handled correctly. When a care giver or family member is not directly available to monitor medication intake, the device can provide a means to do so. Such an application may be additionally preferred when the user or patient is substantially independent but provides added peace of mind to a care giver or family member whose is away.

Additionally included is a bedtime mode. This mode provides a way to dim, silence, or otherwise provide sound and/or a visually discernable display of less impact relative a daytime type display, however still providing important information in case of an emergency.

Additionally, included is an interactive mode, which is designed to interact with the user/patient. It could be used primarily for confirmation of things that might irritate the user, for example if a user is watching a tv program they like, but the device is scheduled to play music as a sound, it is advantageous to receive confirmation from the user before interrupting them, or waking them up for example. Such confirmation may be via voice recognition or wired or wirelessly connected electronic device should the hardware be available to the user.

Still further included is a communication mode, which connects audio and video conferences, such as instantaneous audio and/or video messages. It is best to get confirmation before activating a video camera, or the camera should be placed in a location where it would be fine to see the image at any time, to avoid privacy issues.

Additionally included is a multimedia mode, to play video or audio on a scheduled basis. It may be used for home movies, tv programs, music, or other media available to the user.

With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed device and system herein. It is important, therefore, that the claims be regarded as including such equivalent construction and methodology insofar as they do not depart from the spirit and scope of the present invention.

BRIEF DESCRIPTION OF DRAWING FIGURES

DETAILED DESCRIPTION OF THE PREFERRED

Embodiments of the Invention

Figure 1:
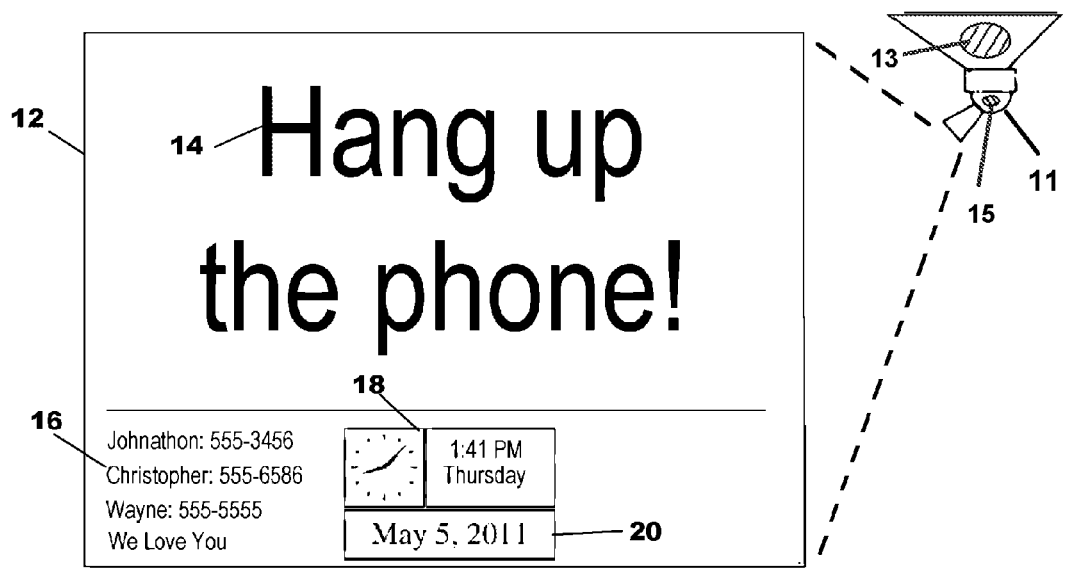
FIG. 1 shows an example of the urgent message mode of the displayed image of the present invention displayed by an overhead projector on a surface.

The present disclosed device 10 and method includes means to display images preferably on a planar surface such as a wall or screen of an indoor location such as the home or residence of the patient user (herein also referred to as recipient 'viewer' or 'patient'), which may be a video display flat screen, or as depicted in the drawings as an overhead projector 11 which will project the image onto a wall surface in place of a flat panel video display which as noted above may also be employed. This is a particularly preferred mode of employing the device 10 because it has been found that patients who are cognitively impaired, or suffer from dementia, tend to try and turn off video screens and televisions which provide them messages or indicia, which if used will need to be connected in a mode wherein they cannot be turned off or disabled.

Thus the display 10 can be a flat panel video display such as a LED or Plasma screen or as described herein the display 10 can be achieved using a digital projector 11. The employment of a digital projector 11 which is adapted to attach to a ceiling or to a ceiling electrical box, places the source of the wall projection of indicia generally out of sight, and out of reach of the patient. In this fashion the display 10 may be either provided by a flat panel video display or may be projected by the overhead projector 11 on any wall in proper range, preferably a surface which the patient is proximate to many times a day.

The positioning of a planar flat screen display as the display 10, which is protected from being deactivated or turned off, or projection of the display 10, from an overhead out-of-reach digital projector 11, provide a display 10 viewable by the patient which is not easily deactivated. If a patient or user is not suffering from dementia or cognitive impairment at a level that prohibits a two-way communication, the display 10 may better server the patient if is an electronic video display such as a screen of a PC, flat screen television, phone display, etc.

The displayed indicia of text and images are controlled and managed by a remote user (herein also referred to as the 'care giver' or 'family member') over a network using a computer engaged thereto and having software adapted to provide control, communication, and a user-friendly interface for ongoing and real time content management. Generally, a remote user such as a care giver or family member will set up and manage the display 10 of the indicia from the projector 11, or on a flat screen, such as images and text for the intended viewer user such as a young child or elder patient. The patient user at their residence merely receives the displayed indica of text and images and reacts accordingly. As noted, sound can be included to augment the indicia, or in place of the indicia to communicate the message for users who are blind or sight impaired or who understand better with two concurrent means of understanding the message being communicated.

The following disclosure depicts preferred display modes on the positioned display, wherein the indicia of images, texts, and optionally but preferred, sounds, are programmed and controlled remotely by the remote user or additional users, via the interface such as a computer and software adapted to the task and/or through software provided by a website or the like operated by a router providing the interface between the remote projector 11 or connected planar video display, and the inputting computer. The disclosed figures herein show many of the possible display modes wherein indica including images, texts, and videos, and media in the form of sounds, are input to communicate a message to the intended patient user for purposes herein noted such as reminders and real time communications to aid patients suffering from dementia or cognitive impairment. Additional figures herein disclosed depict examples of such a remote located user interface, wherein the content and types of display parameters are set by the user or multiple additional users.

Now referring to drawings in FIGS. 1-10, wherein similar components are identified by like reference numerals, there is seen in FIG. 1 the multimedia indicia and pictorial display 10 positioned or projected on a wall or planar surface, for depiction of indicia such as text and pictures showing the urgent message mode 12. In this urgent message mode 12 indicia in the form of a message depicted as text 14 is shown as the depiction on the display 10 encompassing from ⅔rds to substantially the entire viewing area of the display 10.

It has been found that this oversized type urgent message 12, suddenly taking over the majority of area of the surface of the planar display 10, catches the patient user's attention and thereby provides a means to immediately draw patient user's attention toward the depicted indicia such as the text 14. The indicia may be depicted to show as text 14 and/or images and/or videos, and preferably may also employ a flash and/or be accompanied by media such as sounds from the loudspeaker 13 shown engaged to the projector 11.

It is particularly preferred that this urgent mode 12 employ software adapted to preempt all other modes of electronic depiction of the indicia and communication of sound, as will be disclosed shortly that may be displayed as a means to attract the attention of the patient user, to emphasize the urgency.

The urgent message mode 12 can be connected to sensors communicating over the network which are operatively engaged with other equipment throughout the patient user's residence to initiate the message, and to ascertain that the problem associated with the message 14, has been resolved. For example, in a preferred mode of the system herein, the text 14 depicted on the display 10 may indicate, "Hang up the phone!" A phone-engaged sensor, having detected that the phone has been left off the hook, would cause the urgent message mode 12 to display the message for the duration until the phone receiver is sensed to have been replaced. Once the sensor determines the receiver is on the hook of the phone, the depicted or audible message would cease. Alternatively, however, the remote user or users may prompt such a urgent message mode 12 at any time, via inputting commands to the software on the interface as will be disclosed shortly. This would occur when the remote user determines the patient user has left the phone off the hook.

The display 10 of the urgent message mode 12, if not taking all of the display 10 area, may additionally include static information 16, 18, 20 that remains on the display 10. Such information can be, but is not limited to, text 16 which includes information from a group including person's names, phone numbers, and messages, current digital and analog time 18, as well as indicia concerning current date information 20.

Figure 2:
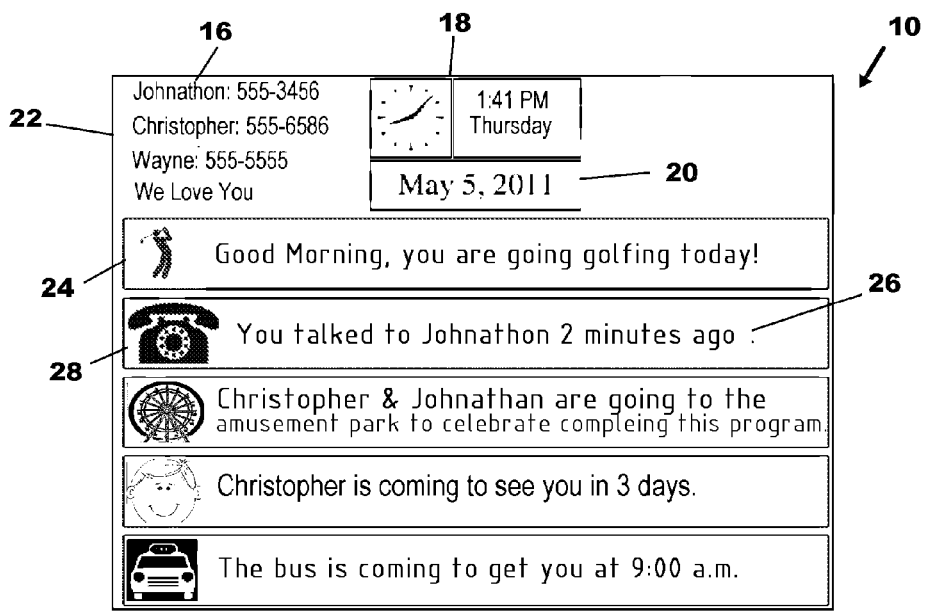
FIG. 2 shows the message board mode of the displayed image of the invention.

Shown in FIG. 2 is another mode of the display 10 showing a message board 22. This mode of the depicted display 10 of a message board 22, shows a plurality of individual messages 24 communicated by indicia including one or a combination of text 26 and images 28. These individual messages 24 are programmed to display from the projector 11 using the remote user software driven interface as will be disclosed shortly. In general, a user will compose messages 24, including typed text 26, and selecting an image 28 to combine the text with, as well as include specific time and date information related to the message.

The interface either running on a remote computer or on a cloud and accessed over a website, will offer the remote user inclusion of the programmed time and date data such that no specific instruction of how and when a message will appear is necessary. For example, "Christopher is coming to see you in 3 days," would automatically generate before and after messages for the programmed time frame. Additionally, there may be a down/up counter used for an anticipated event/visit such as to display the number of days before and after and the message so the patient can enjoy both the anticipation and a reminder of the event. If an audible message is sent over the loudspeaker, as noted, it can employ a family or familiar voice for simple messaging, but may employ a non-familiar commanding voice where an action is required of the patient who it has been shown may respond better to an authoritative voice rather than a family or familiar voice.

Subject inference can be gleaned from the input message, as well, in order to effect the probability of the same topic messages appearing at the same time. This would occur in the background to improve the variety of messages on the display 10. Further, the message board mode 22 may additionally include static information 16, 18, 20 as previously mentioned.

Figure 3:
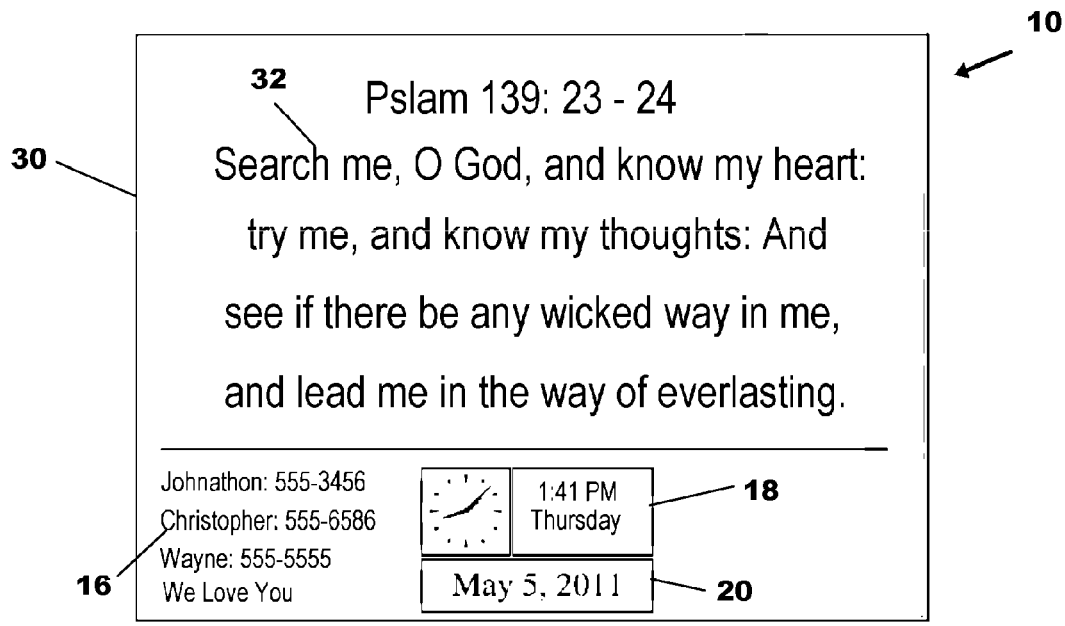
FIG. 3 shows a full screen mode of the displayed image of the invention depicting a line of text.

FIG. 3 shows an intermission full screen mode 30 of depiction on the area of the display 10 with indicia depicting text 32 such as uplifting messages, Bible verses, or any such message as desired. This mode 30 may be provided intermittently between the message board mode 22 and other modes in order to break the monotony of displaying the same mode for an extended period of time, and as a means to attract the attention of the patient user since the change of the indica on the display 10 has been shown to do so. There is further included static information 16, 18, 20 on the display 10 as further reminders to the user.

Figure 4:
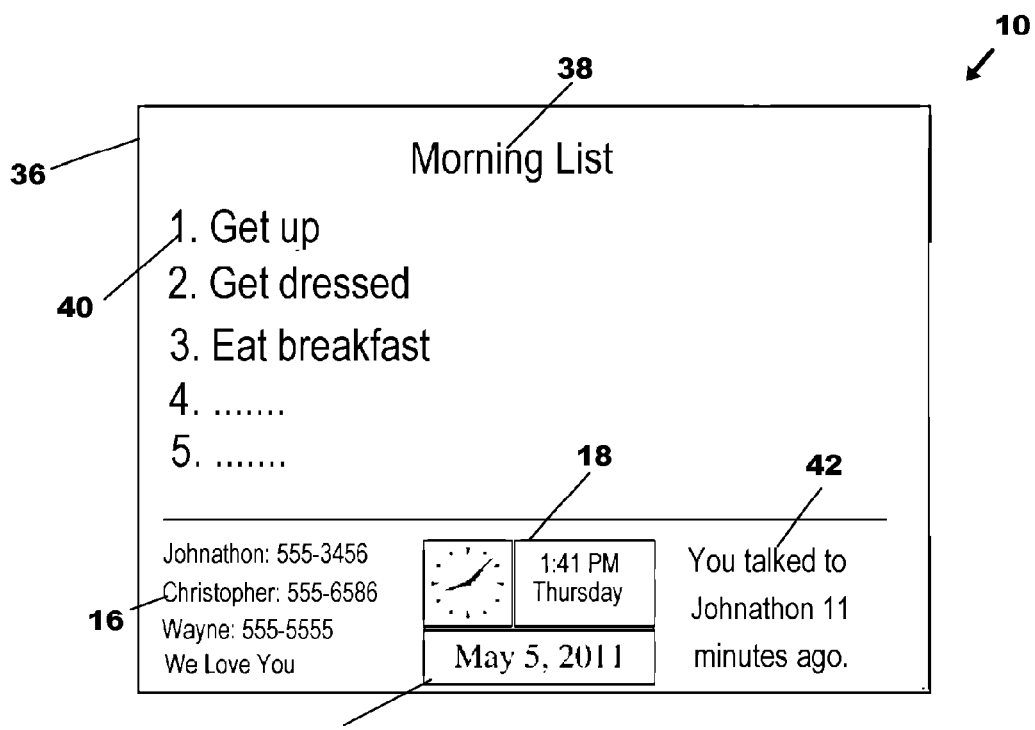
FIG. 4 is another full screen mode of the displayed image of the invention depicting a task list.

FIG. 4 shows an additional task oriented full screen mode 36 displaying indicia on a display 10 concerning task instructions or routines, especially helpful for the cognitively impaired or developmentally disabled, including indicia concerning at least a title 38 and steps list 40. Content may be remote user determined through input in the remote interface, or generated by an interface computer and can be directed to be displayed at remote user specified times and duration. This mode may similarly display intermittently with the message board mode 22 or other modes as desired. Again, for visually impaired patients, a voice announcing the message can concurrently be communicated and broadcast over the loudspeaker.

Adjacent the static information 16, 18, 20 is an dynamically changing phone call notification message 42. This message 42 may be input by the remote user such as a care giver or other user immediately following their phone call with the patient user, as a reminder to the patient user. Alternatively, the software running remotely to control indicia from the area of the positioned display 10, may be integrally connected to the home or cell phone of the remote user, such as an "app", and operate to automatically generate a notification message 42.

It must be noted that the phone call notification message 42 can appear in any of the modes of the area of the display screen or projected display 10 and is not limited to the full screen mode 36. Furthermore, the message 42 duration may be user determined or employ set values such as displaying up to 15 minutes after a phone call for example. This notification message 42 has been found to be of great help to patient users suffering from dementia who tend to telephone caretakers dozens of times a day, not realizing they just spoke to them within a few minutes.

Consequently means to cause the notification message 42 to automatically generate, immediately after a telephone call between a remote user and the patient user, such as a software application running on the phone, which communicates to and through the software running remotely on a server, computer, or website, to cause the projector 11 or electronic video display, to display the notification message 42 of the phone call with the respective remote user.

Figure 5:
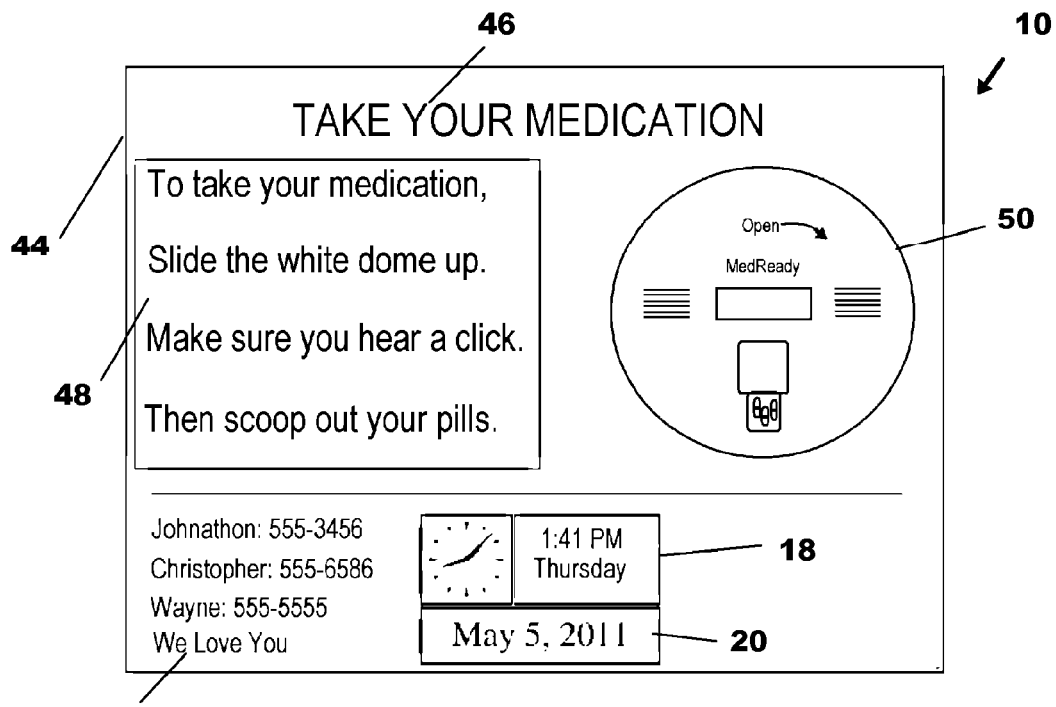
FIG. 5 shows the medication mode of the displayed image of the invention.

FIG. 5 shows the medication mode 44 of the depicted display 10. There is seen a title 46 indicating the task needed to be completed such as taking the medication, as is dictated via instruction in text 48. It is desirable to keep such text short and concise as it will allow for easy understanding by the viewer. There may additionally be included an image 50 related to the task of taking the medication such as a picture of the exact medication to take and at what quantity. Additionally an audible communication of text 48 can concurrently be communicated so the patient can both view and hear the message.

Preferably, the system, may additionally be wired or wirelessly connected to a medication dispensing device (not shown), which ascertains the taking of the medicine which was the subject of the text 48 in the medication mode 44. Using software adapted to the task, the confirmation of the taking of the medicine would be communicated over a network to the server or computer or website controlling the video display or display of the projector 11 to cause the medication mode 44 to cease.

Additionally, another preferred means for confirmation of taking of the medication of the subject medication mode 44 can include a means for the patient user to communicate an oral confirmation response, such as a voice affirmation or the like which is picked up by the microphone 15 engaged to a microprocessor and modem or other hardware, that communicates the response to a remote care giver or family member's phone, PC, etc. over the network, to provide an oral confirmation that the medication has been taken.

Figure 6:
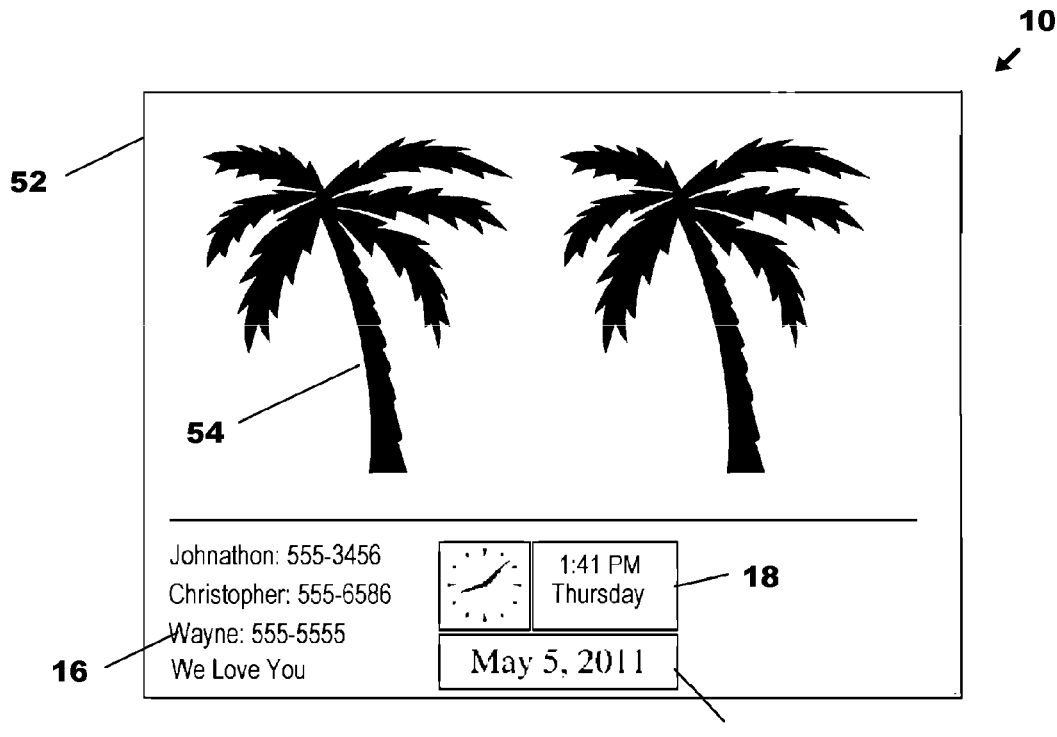
FIG. 6 is yet another full screen mode of the displayed image of the invention depicting a picture.

An additional full screen mode 52 of the video screen display 10 or projected display 10 is shown in FIG. 6 depicting the display 10 displaying indicia of an image 54 such as a picture or the like. A remote user such as a care giver or family member can upload photographs using software adapted to the task running on the computer, server, or website, which will communicate them over the network to the engaged projector 11 and cause them to be displayed in the full screen mode 52. This can provide friendly reminders to the viewer that they are thought of and loved. There is additionally shown static information 16, 18, 20. Optionally a concurrent communication of an audible message of the indicia in the image 54 can be provided.

Figure 7:
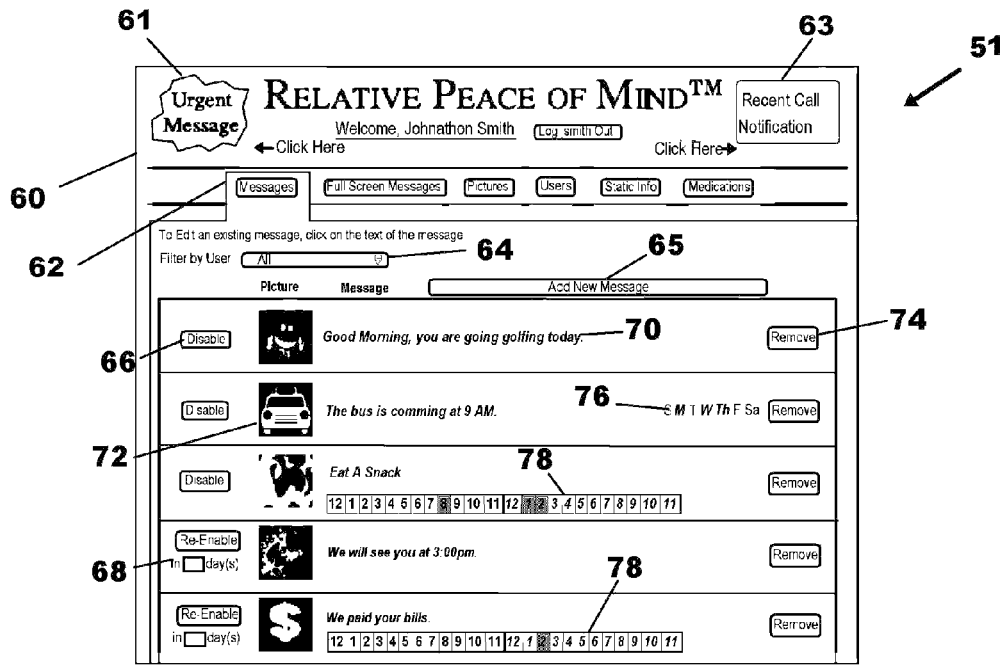
FIG. 7 is an home interface window for editing the content of the displayed images of the invention such as a website or similar interface.
Figure 8:
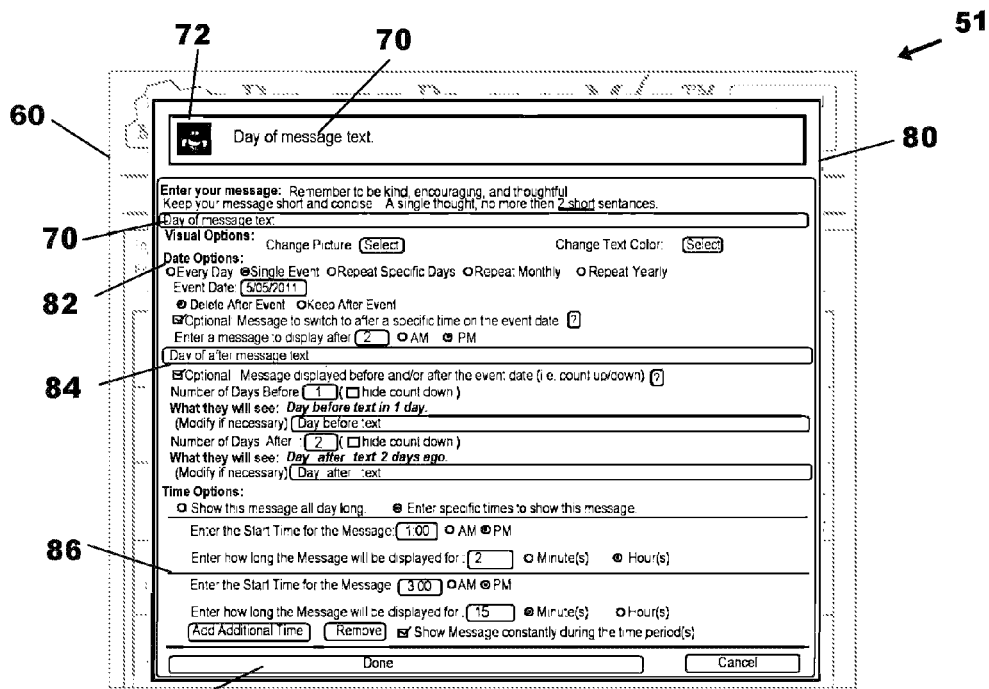
FIG. 8 shows an additional interface window for editing the message board content.
Figure 9:
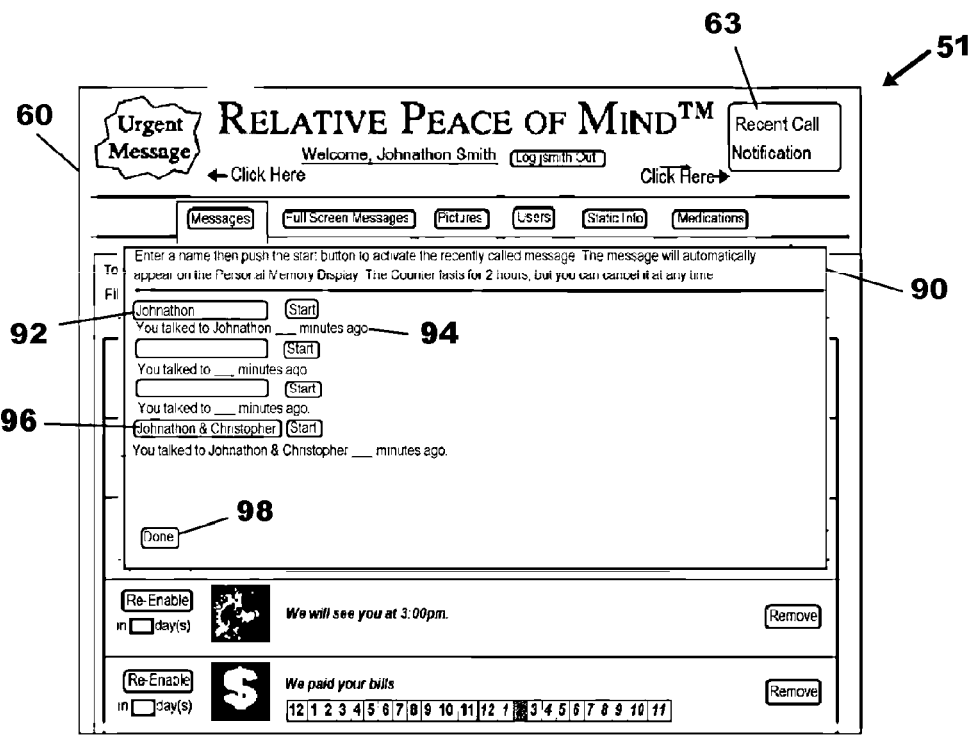
FIG. 9 shows another interface window for editing the call notification content.
Figure 10:
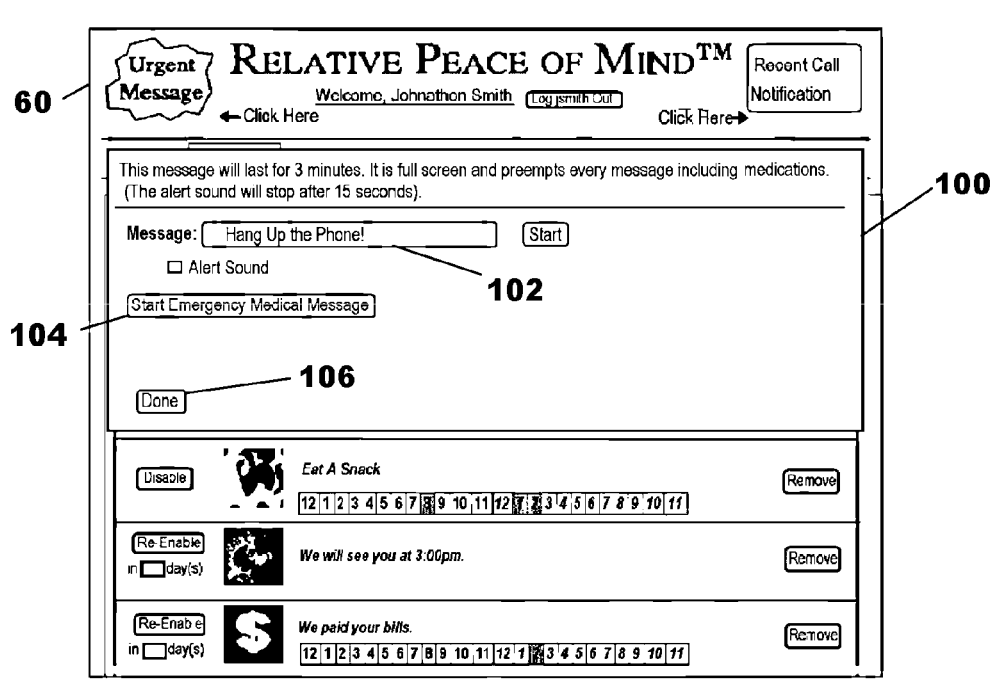
FIG. 10 is still another interface window for editing the urgent message content.

FIG. 7 shows a typical view of the software-generated user interface 51 home window 60 on a remote user's display screen. Such an interface 51 may be accessed by a care giver running on the care giver's own computer or smart phone, on a server or computer via a website over the internet, or other means such as a local connection. In general, a remote user can access and manage content of the modes of the depicted images and indicia and the like on the display 10 via a plurality of tabs 62 as well as buttons 61, 63 linked to additional pop up interface windows (FIGS. 8-10). As shown in the figure, the "message" tab 62 allows a user to create 65 and edit messages in real time for the message board mode 22 previously disclosed. Messages generally include text 70 and corresponding picture 72.

Various controls allow a user means to disable current messages 66, as well as set enabling message parameters 68. Users may additionally remove currently set messages 74. Further, messages can be scheduled to appear at specific times or repeating times during the day 78; on separate days

76 including bi-weekly, weekly, every other week, on repeating days, months, or years etc.

When creating new messages 65, an additional interface window 80 will appear as shown in FIG. 8. As can be seen the additional window 80 appears above the home interface 60 such that the home interface 60 remains substantially transparent indicating the additional window 80 is being operated.

Again, information can be input with a selection of pictures, text color, display times, scheduled time for display including multiple days, weeks, biweekly, monthly, yearly etc. 82. It is preferred that all messages can be entered or edited 24 hours per day. Messages can be time specific 86 and take precedent over general messages. A single message can have a "before, current, after" event display message 84 that counts up/down according to the number of display days selected. Preferably the display 10 shows five messages per screen, but can display fewer if the person has vision problems wherein the print increases in size on the display 10. All input information can then be saved and confirmed by the user 88. Optionally, the messages can be communicated in an audible fashion to the patient using software widely available which converts text words to voice communications which can be concurrently broadcast over the loudspeaker to the patient.

FIG. 9 shows the aforementioned call notification 42 interface window 90 depicted over the home interface window 60 for inputting and setting a call notification message 42. Individual 92 or multiple 96 names can be inputted and shown as it is to be read 94 by the patient on the flat panel video or projected display 10. Again, a user then can save and confirm the information inputted 98. The counter of the message 42 is preferably automatic and starts when a remote user confirms the information inputted. As noted, an application running on the remote user's phone can also communicate with the server, or computer running the software, and cause the call notification 42 to be communicated to and displayed as indicia on the display 10 by the projector 11.

FIG. 10 shows the urgent message interface window 100 wherein urgent message text 102 is inputted as will be displayed in the urgent message mode 12. Additional urgent messages 104, such as medical emergencies, can also be employed. Again, the user confirms and saves the information 106.

As noted, the projector 11, or video display, has or is engaged to hardware such as a modem, and employs software to receive the indicia to be depicted on the video display or projected onto a wall or flat surface. Communication may be wireless, wired, or other means of conventional communication between remote computing devices and display devices. In modes employing the projector 11, it is preferably ceiling mounted to place it out of the reach of the patient users, and is configured to project the indicia on a flat surface or wall of the residence which is proximate to the patient user on a frequent basis. In modes where a flat screen display is employed, it is preferable that the power switch be disabled or the patient otherwise prevented from tampering with the electronic display screen. In this fashion, the patient user is provide with a tamper proof means for generating and depicting discernable indicia of text and pictures and video, which will help the remote patient user function in their daily lives.

Communication of the indicia to the video screen or respective projectors 11 projecting a display 10 located in patient-users residences is best handled through the server of the system provider. If employed, the projector 11 would be placed on a ceiling in the residence of a patient user, and communications over a network such as the internet would be established between the provider server and the projector. Remote users wishing to communicate and check on a patient user would employ software, adapted to operate on a computer or smart phone, to communicate through the server providing the interface for system operation, and choose the indicia to be displayed on the display 10 area by the projector 11 of their respective relative or loved one who is a patient user. Where a flat screen or other electronic video display is employed, such would be wireless or wired in a fashion to prevent tampering.

Operations of the system requiring confirmation of a task, or the recent placing of a phone call, will employ sensors also adapted to those respective tasks communicating over the network when needed. Thus, the phone of a remote user such as a relative ending a phone call with a patient user, will have software running thereon configured to send a signal of the cessation time of a phone call with the patient user to the server whereafter the notification message would be generated without the need for the remote user's input on the system. The same sensor and signal over the network operation can be employed to automatically notify the remote users that the patient user has taken one or more medications as noted above.

While all of the fundamental characteristics and features of the invention have been shown and described herein, with reference to particular embodiments thereof, a latitude of modification, various changes and substitutions are intended in the foregoing disclosure and it will be apparent that, in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

The invention claimed is:
1. A system providing continuous indicia viewable by a recipient for reminder and action-inducing, comprising:
   a remote computing device employable by a remote user;
   an interface computing device;
   a video display located at an indoor location occupied by said recipient;
   a network, said network engaged to transmit and receive digital communications between said remote computing device, said interface computing device and said video display;
   said remote computing device having software configured for transmitting indica generated from text input by said remote user, and from images chosen by said remote user from images stored on said remote computing device, combined in a said digital communication;
   said video display configured to depict a display of said indicia within a viewing area proximate to said recipient, said display of said indicia, employing solely said digital communication from said remote computing device;
   said video display configured to continuously depict said display of said indicia in said viewing area for a duration of time determined by said remote user prior to cessation of said digital communication, and without consent or required action on the part of said recipient;

said display of indicia including displayed messages generated from said text input by said remote user and being managed by said remote user on said remote computing device whereby said display of indicia including said displayed messages and said images, will continuously display within said display of said indicia for said duration of time subsequent to cessation of said digital communication from said remote computing device of said user.

2. The system providing continuous indicia of claim 1 additionally comprising:
said viewing area being positioned upon a vertically disposed wall.

3. The system providing continuous indicia of claim 2 additionally comprising:
said viewing area being on said video display wherein said video display comprises a projection upon said wall from a video projector.

4. The system providing continuous indicia of claim 3 additionally comprising:
said projection device configured for positioning upon a roof or ceiling of a room at said indoor location, elevated above said recipient;
said projection device configured to display said display of said indicia upon a wall of said room; and
said positioning elevated above said recipient and said projection of said display of said indicia upon said wall, providing means to prevent said recipient from a tampering with said projection device which might cause a termination or a disabling of said display of said indicia.

5. The system providing continuous indicia of claim 2 additionally comprising:
said viewing area being upon a said video display comprising an electronic video display screen, positioned upon said wall.

6. The system providing continuous indicia of claim 2 additionally comprising:
said display of indicia in said viewing area positioned on said wall, providing means to position said displayed messages at a position in said room determined to be occupied by said recipient at a high percentage of a day said recipient, thereby providing means to insure said recipient views said messages.

7. The system providing continuous indicia of claim 6 additionally comprising:
said display of indicia in said viewing area upon said wall including text listing one or a plurality names of callers, who have telephoned said recipient on said telephone; and
said listing providing means to remind a cognitively impaired patient of an identity of said callers.

8. The system providing continuous indicia of claim 6 additionally comprising:
said remote computing device configured to communicate sound over said network to a loudspeaker at said indoor location, said sound being a concurrent audible communication of words in said displayed messages.

9. The system providing continuous indicia of claim 8 additionally comprising:
said displayed messages include reminder text providing a reminder to said patient to take medication, whereby said system displaying said reminder text provides means to induce said patient to timely ingest their medications.

10. The system providing continuous indicia of claim 8 additionally comprising:
said displayed messages including a listing of tasks said recipient must accomplish, whereby said recipient is reminded of said tasks as a means of enabling a cognitively impaired said recipient to live at said indoor location with a minimum of oversight by third parties.

11. The system providing continuous indicia of claim 6 additionally comprising:
said displayed messages including reminder text input in said text input by said remote user, said reminder text providing a reminder to said patient to take medication, whereby said system provides means to induce said patient to timely ingest their medications.

12. The system providing continuous indicia of claim 6 additionally comprising:
said displayed messages including a listing of tasks said recipient must accomplish, whereby said recipient is reminded of said tasks as a means of enabling a cognitively impaired said recipient to live at said indoor location with a minimum of oversight by third parties.

13. The system providing continuous indica of claim 6 additionally comprising:
a microphone located at said indoor location;
software configured to receive oral input from said patient through said microphone and transmit it to one or both of said interface and said remote computing device;
said oral input so transmitted providing means for said patient to provide oral responses to said displayed messages.

14. The system providing continuous indicia of claim 2 additionally comprising:
a sensor located at said indoor location, said sensor monitoring a position of a telephone handset;
said sensor in communication with said remote computing device;
said remote computing device configured to generate a reminder message and communicate said reminder message to be included within said display of said indicia, said reminder message being instructions to hang up said telephone should said sensor communicate a signal to said remote computing device over said network, indicating said telephone handset of off the hook.

15. The system providing continuous indicia of claim 2 additionally comprising:
said remote computing device configured to communicate sound over said network to a loudspeaker at said indoor location, said sound being a concurrent audible communication of words in said displayed messages.

16. The system providing continuous indicia of claim 1 additionally comprising:
said remote computing device configured to communicate sound over said network to a loudspeaker at said indoor location, said sound being a concurrent audible communication of words in said displayed messages.

17. The system providing continuous indicia of claim 1 additionally comprising:
said displayed messages including a clock, said clock depicting a current time at said indoor location.

* * * * *